US008835601B2

(12) United States Patent
Chen et al.

(10) Patent No.: US 8,835,601 B2
(45) Date of Patent: Sep. 16, 2014

(54) NATRIURETIC POLYPEPTIDE DELIVERY SYSTEMS

(71) Applicants: Mayo Foundation for Medical Education and Research, Rochester, MN (US); Nanyang Technological University, Singapore (SG)

(72) Inventors: Horng H. Chen, Rochester, MN (US); John C. Burnett, Jr., Rochester, MN (US); Lim Soo Ghim, Singapore (SG); Subramanian S. Venkatraman, Singapore (SG)

(73) Assignees: Mayo Foundation for Medical Education and Research, Rochester, MN (US); Nanyang Technological University, Singapore (SG)

( * ) Notice: Subject to any disclaimer, the term of this patent is extended or adjusted under 35 U.S.C. 154(b) by 0 days.

(21) Appl. No.: 13/788,309

(22) Filed: Mar. 7, 2013

(65) Prior Publication Data

US 2014/0179605 A1 Jun. 26, 2014

Related U.S. Application Data

(60) Provisional application No. 61/740,652, filed on Dec. 21, 2012.

(51) Int. Cl.
*A61K 38/00* (2006.01)
*A61K 47/34* (2006.01)

(52) U.S. Cl.
CPC ..................................... *A61K 47/34* (2013.01)
USPC ........................... 530/300; 530/324; 530/326

(58) Field of Classification Search
CPC . A61K 45/06; A61K 38/2242; A61K 9/0004; A61K 2300/00; A61K 38/00; A61K 49/0056; A61K 9/0019; C07K 14/58; C07K 17/00; C07K 14/47; C08L 33/26
See application file for complete search history.

(56) References Cited

U.S. PATENT DOCUMENTS 6,407,211 B1 * 6/2002 Burnett et al. ................ 530/350

OTHER PUBLICATIONS

Lambert et al. 1995. J. of Controlled Release 33:189-195.*
Danhier et al. 2012. Jnl of Controlled Release 161:505-522.*
Jain et al. 2000. Europ J. Pharm and Biopharm 50: 257-262.*
Betancourt et al. 2007. Nanomedicine 2:219-232.*
Del Ry, "Radioimmunoassay for plasma C-type natriuretic peptide determination: a methodological evaluation," *Clinical Chemistry and Laboratory Medicine*, 43(6):641-645, Jun. 2005.
Dickey et al., "Novel bifunctional natriuretic peptides as potential therapeutics," *J. Biol. Chem.*, 283(50):35003-35009, print Dec. 2008, Epub Oct. 2008.
Kim and Burgess, "Pharmacokinetic characterization of 14C-vascular endothelial growth factor controlled release microspheres using a rat model," *J. Pharm. Pharmacol.*, 54(7):897-905, Jul. 2002.
Lim et al., "In-Vivo Evaluation of an In Situ Polymer Precipitation Delivery System for a Novel Natriuretic Peptide," PLoS One 8(2): e52484, Feb. 2013.
Lim et al., "Sustained delivery of a novel natriuretic peptide for three weeks with in situ polymer precipitation delivery system," *J Card Fail.*, 18(8):563, Aug. 2012 [abstract].
Lisy et al., "Design, synthesis, and actions of a novel chimeric natriuretic peptide: CD-NP.," J. Am. College Card., 52(1):60-68, Jul. 2008.
Misono et al., "Rat atrial natriuretic factor: isolation, structure and biological activities of four major peptides," *Biochem. Biophys. Res. Comm.*, 123(2):444-451, Sep. 1984.
Padilla et al., "Intravenous administration of the natriuretic peptide urodilatin at low doses during coronary reperfusion limits infarct size in anesthetized pigs," *Cardiovasc. Res.*, 51(3):592-600 Aug. 2001.
Soeki et al., "C-type natriuretic peptide, a novel antifibrotic and antihypertrophic agent, prevents cardiac remodeling after myocardial infarction," *J. Am. Coll. Cardiol.*, 45(4):608-616, Feb. 2005.

* cited by examiner

*Primary Examiner* — Shulamith H Shafer
(74) *Attorney, Agent, or Firm* — Fish & Richardson P.C.

(57) ABSTRACT

This document provides natriuretic polypeptide delivery systems. For example, methods and materials related to natriuretic polypeptide delivery systems, methods and materials related to the use of such delivery systems to deliver natriuretic polypeptides to a mammal over a pro-longed period of time (e.g., weeks to months), and methods and materials related to treating heart failure conditions are provided.

8 Claims, 14 Drawing Sheets

NATRIURETIC POLYPEPTIDE DELIVERY SYSTEMS

CROSS-REFERENCE TO RELATED APPLICATIONS

This application claims the benefit of U.S. Provisional Application Ser. No. 61/740,652, filed Dec. 21, 2012. The disclosure of the prior application is considered part of (and is incorporated by reference in) the disclosure of this application.

STATEMENT AS TO FEDERALLY SPONSORED RESEARCH

This invention was made with government support under grant numbers HL83231 and HL76611 awarded by the National Institutes of Health. The government has certain rights in the invention.

BACKGROUND

1. Technical Field

This document relates to natriuretic polypeptide delivery systems. For example, this document provides methods and materials related to natriuretic polypeptide delivery systems and methods and materials related to the use of such delivery systems to deliver natriuretic polypeptides to a mammal over a pro-longed period of time (e.g., weeks to months) to treat conditions such as cardiovascular disease, heart failure, coronary artery disease, myocardial infarction, hypertension, diabetes, and renal failure.

2. Background Information

There are various methods that can be adopted for the treatment of heart failure (HF) conditions. One of the ways is to administer exogenous natriuretic polypeptides (NPs) into HF patients. Several synthetic versions of naturally-occurring NPs have been developed and tested.

Presently, these polypeptides are administered intravenously while HF patients are hospitalized. However, despite the improvements in HF symptoms as a result of the treatment during hospitalization, there is still a high occurrence of re-admission and mortality rate associated with discharged patients. Currently, the only way to administer NPs chronically, in a non-clinical setting, is subcutaneous (SQ) bolus administration due to the short half-life of NPs.

SUMMARY

This document provides natriuretic polypeptide delivery systems. For example, this document provides methods and materials related to natriuretic polypeptide delivery systems, methods and materials related to the use of such delivery systems to deliver natriuretic polypeptides to a mammal over a pro-longed period of time (e.g., weeks to months), and methods and materials related to treating heart conditions such as cardiovascular disease, heart failure, coronary artery disease, myocardial infarction, hypertension, diabetes, and renal failure.

As described herein, polymer gel compositions containing NPs can be designed to include one or more NPs at a concentration and in an environment that (a) protects the NPs from degradation over a period of time (e.g., a period of time longer than 2, 3, 4, 5, or more weeks) when within a mammal and (b) releases therapeutic levels of the NPs from the composition into the mammal's circulation over a period of time (e.g., a period of time greater than 2, 3, 4, 5, or more weeks). For example, a composition (e.g., a gel composition) provided herein can be formed using one or more polymer materials such as poly(lactic-co-glycolic acid) (PGLA), poly(L-lactic acid) (PLLA), poly(D-lactic acid) (PDLA), poly(D,L-lactic acid) (PDLLA), poly(glycolide), or poly(ethylene glycol) (PEG), one or more solvents such as N-methyl-2-pyrrolidinone (NMP), triacetin, or dimethyl sulfoxide (DMSO), and one or more NPs such as ANP, BNP, CNP, CD-NP, URO, DNP, mANP, ABC-NP, ABC-NP1, or CU-NP such that the NPs are protected from degradation over a period of time (e.g., a period of time longer than 2, 3, 4, 5, or more weeks) when within a mammal and are released at therapeutic levels from the composition into the mammal's circulation over a period of time (e.g., a period of time greater than 2, 3, 4, 5, or more weeks). Such compositions can be used to treat heart failure conditions as well as other conditions such as cardiovascular disease, coronary artery disease, myocardial infarction, hypertension, diabetes, and renal failure outside of hospital settings without continuous administration or frequent administrations (e.g., daily, every other day, or weekly administrations).

In general, one aspect of this document features a polymer gel composition comprising, or consisting essentially of, a natriuretic polypeptide, poly(lactic-co-glycolic acid), and a solvent. The natriuretic polypeptide can be CD-NP. The natriuretic polypeptide can comprise the amino acid sequence set forth in one of SEQ ID NOs:1-10. The solvent can be N-methyl-2-pyrrolidinone or triacetin. The composition can comprise N-methyl-2-pyrrolidinone and triacetin. The intrinsic viscosity of the poly(lactic-co-glycolic acid) can be between 0.015 and 3 dL/g. The composition can comprise from about 0.1 percent and 0.5 percent of the natriuretic polypeptide. The composition can comprise from about 15 percent and 45 percent of the poly(lactic-co-glycolic acid). The composition can comprise from about 15 percent and 25 percent of the poly(lactic-co-glycolic acid). The composition can comprise from about 1 percent and 10 percent of triacetin. The composition can lack triacetin. The composition can comprise acid capped poly(lactic-co-glycolic acid).

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1A is a graph plotting the in vitro release of CD-NP as the percent of cumulative drug release over 31 days from a gel formulation. FIG. 1B is graph plotting the in vitro release of CD-NP as the estimated daily amount of drug release over 31 days from a gel formulation.

FIGS. 2A1, 2A2, 2B1, and 2B2 are graphs plotting the blood pressure fluctuation over 18 days for CD-NP treatment groups and vehicle groups. FIG. 2A1 is a graph plotting the blood pressure trend for the CD-NP treatment group. FIG. 2A2 is a graph plotting a magnified view of 3 days for the treatment group. FIG. 2B1 is a graph plotting the blood pressure trend for the vehicle group. FIG. 2B2 is a graph plotting a magnified view of 3 days for the vehicle group. All time points are significantly different except for day 0 and day 12 when comparing blood pressure values between treatment and vehicle groups at the same time point.

DETAILED DESCRIPTION

Figure 1:
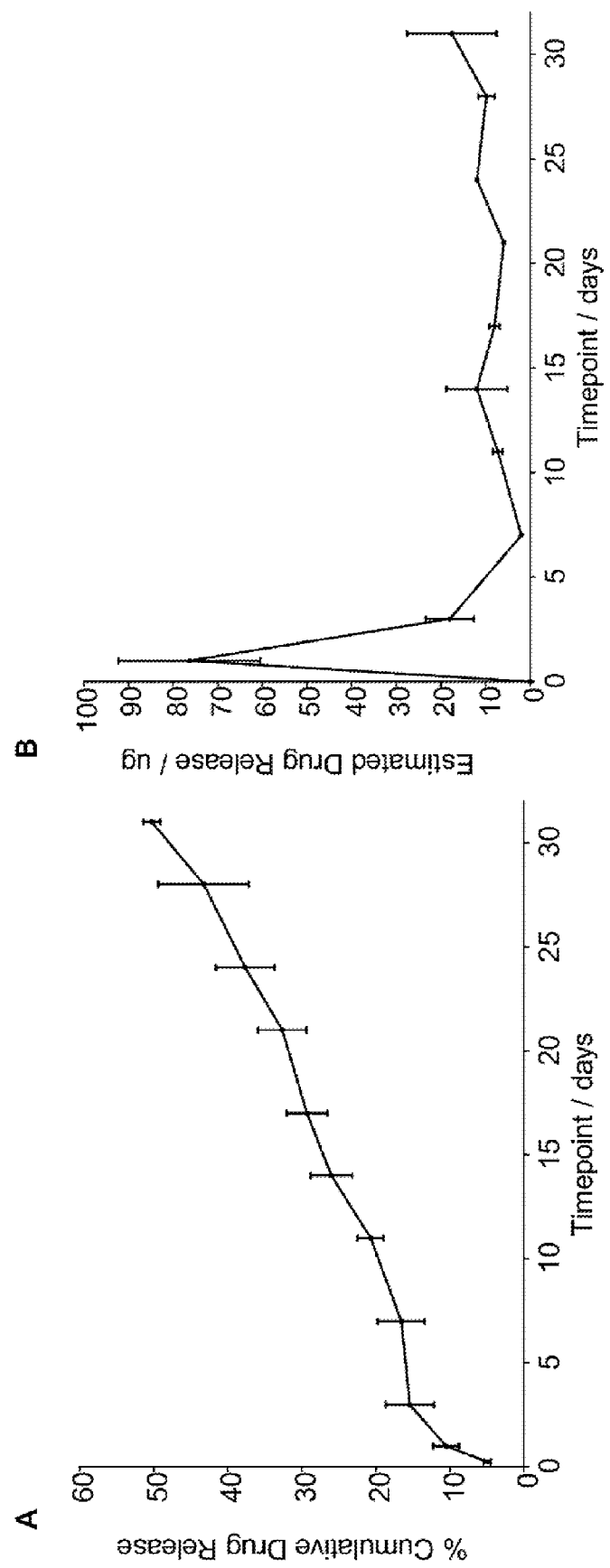

This document provides natriuretic polypeptide delivery systems. For example, this document provides methods and materials related to natriuretic polypeptide delivery systems, methods and materials related to the use of such delivery systems to deliver natriuretic polypeptides to a mammal over a pro-longed period of time (e.g., weeks to months), and methods and materials related to treating conditions such as cardiovascular disease, heart failure, coronary artery disease, myocardial infarction, hypertension, diabetes, and renal failure.

A polymer gel composition provided herein can contain a natriuretic polypeptide and can be designed to create an environment that releases therapeutic levels of the natriuretic polypeptide into a mammal's circulation over a period of time (e.g., a period of time greater than 2, 3, 4, 5, or more weeks) when injected into the mammal. For example, a composition (e.g., a gel composition) provided herein can be formed using one or more polymer materials, one or more solvents, and one or more natriuretic polypeptides. Examples of polymer materials that can be used to make a polymer gel composition provided herein include, without limitation, poly(lactide-co-glycolide) (PGLA), poly(L-lactic acid) (PLLA), poly(D-lactic acid) (PDLA), poly(D,L-lactic acid) (PDLLA), poly(glycolide), and poly(ethylene glycol) (PEG). In some cases, a polymer material used to make a polymer gel composition provided herein can have an intrinsic viscosity that is from about 0.015 dL/g to about 3 dL/g (e.g., from about 0.015 dL/g to about 2.5 dL/g, from about 0.015 dL/g to about 2 dL/g, from about 0.015 dL/g to about 1 dL/g, from about 0.015 dL/g to about 0.5 dL/g, from about 0.015 dL/g to about 0.75 dL/g, from about 0.015 dL/g to about 0.5 dL/g, from about 0.05 dL/g to about 3 dL/g, from about 0.1 dL/g to about 3 dL/g, from about 0.2 dL/g to about 3 dL/g, from about 0.3 dL/g to about 3 dL/g, from about 0.1 dL/g to about 1 dL/g, or from about 0.1 dL/g to about 0.8 dL/g). Examples of solvents that can be used to make a polymer gel composition provided herein include, without limitation, NMP, triacetin, and DMSO. Examples of natriuretic polypeptides that can be used to make a polymer gel composition provided herein include, without limitation, ANP, BNP, CNP, CD-NP, URO, DNP, mANP, ABC-NP, ABC-NP1, or CU-NP. The amino acid sequence of such natriuretic polypeptides can be as set forth in Table 1.

TABLE 1

Natriuretic polypeptides.

| Natriuretic polypeptide | Sequence | SEQ ID NO: |
|---|---|---|
| ANP | SLRRSSCFGGRMDRIGAQSGLGCNSFRY | 1 |
| BNP | SPKMVQGSGCFGRKMDRISSSSGLGCKVLRRH | 2 |
| CNP | GLSKGCFGLKLDRIGSMSGLGC | 3 |
| URO | TAPRSLRRSSCFGGRMDRIGAQSGLGCNSFRY | 4 |
| DNP | EVKYDPCFGHKIDRINHVSNLGCPSLRDPRP NAPSTSA | 5 |
| CU-NP | TAPRSLRRSSCFGLKLDRIGSMSGLGCNSFRY | 6 |
| CD-NP | GLSKGCFGLKLDRIGSMSGLGCPSLRDPRPN APSTSA | 7 |
| mANP | SLRRSSCFGGRMDRIGAQSGLGCNSFRYRRI TAREDKQGWA | 8 |
| ABC-NP | RMDRIGLSKGCFGLKLDRIREASGLGCKVLR RH | 9 |
| ABC-NP1 | RMDRIGLSKGCFGLKLDRIGSMSGLGCKVLR RH | 10 |

A polymer gel composition provided herein can contain any appropriate amount of natriuretic polypeptide, polymer material, and solvent. For example, a polymer gel composition provided herein can contain from about 0.0001 percent to about 99 percent (e.g., from about 0.1 percent to about 30 percent, from about 0.1 percent to about 20 percent, from about 0.1 percent to about 10 percent, from about 0.1 percent to about 5 percent, from about 0.25 percent to about 40 percent, from about 0.5 percent to about 40 percent, from about 0.75 percent to about 40 percent, from about 1 percent to about 40 percent, from about 0.25 percent to about 10 percent, or from about 0.25 percent to about percent) of natriuretic polypeptide (e.g., CD-NP). In some cases, a polymer gel composition provided herein can contain from about 0.0001 percent to about 99 percent (e.g., from about 5 percent to about 40 percent, from about 5 percent to about 35 percent, from about 5 percent to about 30 percent, from about 5 percent to about 20 percent, from about 10 percent to about 40 percent, from about 15 percent to about 40 percent, from about 20 percent to about 40 percent, from about 15 percent to about 35 percent, from about 15 percent to about 30 percent, or from about 15 percent to about 25 percent) polymer material. In some cases, a polymer gel composition provided herein can contain from about 0.0001 percent to about 99 percent (e.g., from about 20 percent to about 95 percent, from about 20 percent to about 90 percent, from about 20 percent to about 85 percent, from about 20 percent to about 80 percent, from about 20 percent to about 75 percent, from about 25 percent to about 95 percent, from about 35 percent to about 95 percent, from about 40 percent to about 95 percent, from about 70 percent to about 90 percent, or from about 75 percent to about 85 percent) solvent.

In some cases, a polymer gel composition provided herein can be used to treat conditions such as cardiovascular disease, heart failure, coronary artery disease, myocardial infarction, hypertension, diabetes, and renal failure. In some cases, a polymer gel composition provided herein can be used to increase natriuretic activity in a subject in need thereof. Examples of natriuretic activities that can be increased using a polymer gel composition provided herein include, without limitation, increases in plasma cGMP levels, urinary cGMP excretion, net renal cGMP generation, urine flow, urinary sodium excretion, urinary potassium excretion, hematocrit, plasma BNP immunoreactivity, renal blood flow, and/or plasma ANP immunoreactivity. In some cases, a polymer gel composition provided herein can be used to decrease renal vascular resistance, proximal and distal fractional reabsorption of sodium, mean arterial pressure, pulmonary capillary wedge pressure, right atrial pressure, pulmonary arterial pressure, plasma renin activity, plasma angiotensin II levels, plasma aldosterone levels, renal perfusion pressure, and/or systemic vascular resistance. In some cases, a polymer gel composition provided herein can be used to treat, inhibit, and/or prevent cardiac remodeling and ischemia-reperfusion injury, particularly after acute myocardial infarction (AMI) and/or acute heart failure (AHF). For example, a polymer gel composition provided herein can be used to increase plasma cGMP, which may be desirable for applications in attenuating myocardial ischemia-reperfusion injury (Padilla et al., *Cardiovasc. Res.*, 51:592-600 (2001)).

A polymer gel composition provided herein can be administered by a number of methods, depending upon whether local or systemic treatment is desired. Administration can be, for example, by injection. In some cases, polymer gel composition provided herein can be injected into the subcutaneous tissue, or intradermal or intramuscular tissue of a mammal (e.g., a human). A polymer gel composition provided herein for injection can include, without limitation, sterile aqueous solutions (e.g., sterile physiological saline), buffers, diluents, additives (e.g., penetration enhancers, carrier compounds, and other pharmaceutically acceptable carriers), thickeners, colorings, flavoring agents, emulsifiers, lubricants, preservatives, stabilizers, salts for influencing osmotic pressure, wetting agents, dispersing aids, anti-pruritics, astringents, local anesthetics, anti-inflammatory agents, and/or binders. When added, however, such materials should not unduly interfere with the biological activities of the other components within the polymer gel composition (e.g., the natriuretic polypeptides).

A polymer gel composition provided herein can be presented conveniently in unit dosage form. Such techniques can include the step of bringing into association an active ingredient (e.g., a natriuretic polypeptide) with the desired polymer material. A polymer gel composition provided herein can be sterilized if desired, provided that the method of sterilization does not interfere with the effectiveness of the polymer gel composition.

This document also provides methods for using a polymer gel composition provided herein to treat, for example, treat heart failure conditions. For example, a polymer gel composition provided herein can be administered to a mammal (e.g., a human or a non-human mammal) in order to increase plasma natriuretic polypeptide levels and plasma cGMP levels. In some embodiments, for example, a polymer gel composition provided herein can be administered to a mammal diagnosed as having cardiovascular disease, heart failure, coronary artery disease, myocardial infarction, hypertension, diabetes, or renal failure. A polymer gel composition provided herein can be administered at any suitable dose, depending on various factors including, without limitation, the agent chosen, the severity of the disease, and whether prevention or treatment is to be achieved. Administration can be local or systemic.

In some embodiments, a polymer gel composition provided herein can be administered at a dose of at least about 0.01 ng natriuretic polypeptide/kg to about 100 mg natriuretic polypeptide/kg of body mass (e.g., about 10 ng natriuretic polypeptide/kg to about 50 mg natriuretic polypeptide/kg, about 20 ng natriuretic polypeptide/kg to about 10 mg natriuretic polypeptide/kg, about 0.1 ng natriuretic polypeptide/kg to about 20 ng natriuretic polypeptide/kg, about 3 ng natriuretic polypeptide/kg to about 10 ng natriuretic polypeptide/kg, or about 50 ng natriuretic polypeptide/kg to about 100 μg/kg) of body mass, although other dosages also may provide beneficial results. In some cases, a polymer gel composition provided herein can be administered to a first location (e.g., a subcutaneous tissue of the abdominal wall of a mammal) for a first administration, and then can be administered via another location (e.g., a subcutaneous tissue of the buttocks region of a mammal) for a second administration.

The invention will be further described in the following example, which does not limit the scope of the invention described in the claims.

EXAMPLES

Example 1

Sustained Delivery of Natriuretic Polypeptides for Three Weeks with In Situ Polymer Precipitation Delivery System 0.45% percentage weight/weight (w/w) of CD-NP was mixed with 40% poly(lactic-co-glycolic acid) in 39.55% (w/w) N-methyl-2-pyrrolidinone and 20% (w/w) triacetin. The resulting mixture was allowed to homogenize overnight. Three groups of 5 rats (Wistar male, 250-300 g) were injected subcutaneously with the gel. A fourth group (n=5) was injected with blank gels as vehicles. Rats sacrificed at respective time points (1 week, 2 weeks, or 3 weeks) for plasma and urinary evaluation.

Plasma CD-NP levels were significantly higher than vehicle: 32,700±2888 pg/mL, 13,977±3302 pg/mL, and 7,566±1115 pg/mL at weeks 1, 2, and 3 after gel injection. 24-hour urinary CD-NP excretion levels were significantly elevated at 107.3±12.7 pg/minute, 33.7±29.7 pg/minute, and 16.5±8.2 pg/minute at weeks 1, 2, and 3 as compared to 2.02±0.10 pg/minute pre-injection. No significant difference was observed before and 3 weeks after gel injection in the vehicle group. Plasma cGMP levels were significantly elevated at 271.0 pmol/mL±41.4 at week 1 with a trend to be higher at weeks 2 and 3 as compared to vehicle. 24-hour urinary cGMP output was significantly elevated to 57.7±2.9 pmol/minute and 56.6±7.4 pmol/minute at week 1 and 2 as compared to pre-injection.

These results demonstrate that gel formulations can be designed to release CD-NP for sustained time periods such as those over 3 weeks.

Example 2

In Vivo Evaluation of an In Situ Polymer Precipitation Delivery System for Natriuretic Polypeptides Materials Poly D,L-lactic-co-glycolic acid (PLGA) (17 kDa, 50:50 dl-LA to GA ratio, inherent viscosity: 0.2 dL/g; obtained from Purac Biomaterials, Gorinchem, Netherlands) was used to form gel formulations. HPLC grade N-methyl-2-pyrrolidinone (NMP; obtained from Sigma Aldrich) and triacetin (obtained from Fisher Scientific) were used as solvents. Both solvents were of low toxicity. CD-NP polypeptide preparations were obtained from Nile Therapeutics, Inc.

Synthesis of In Situ Polymer Precipitation Delivery System

Preparation of the injectable gel formulation was as followed. Briefly, CD-NP was dissolved in NMP solvent, and the resulting suspension was allowed to stir for at least 3 to 4 hours before the addition of pre-weighed polymer and triacetin solution. The quantities added were such that the polymer and triacetin content was 40% and 20% by weight, respectively, with the CD-NP being present at 0.45% (w/w). The final solution was allowed to homogenize overnight. Fresh gel samples were prepared one day in advance of each injection.

In Vitro Studies

Before in vivo evaluation, several gel formations were tested in vitro. Effects of different gel parameters namely polymer concentration, single and co-solvent systems, NMP/Triacetin concentration, CD-NP drug loading, and gel injected volume were investigated (see, e.g., Example 3). Factors such as gel viscosity, which can influence syringeability, initial burst levels of drug from the gel system, and the ability to have a linear release profile during the first three to four weeks were assessed.

Briefly, 0.7 cc of gel was injected into 10 mL of PBS buffer (pH 7.4) through a 20 G needle. Sample vials were placed on a 3-ways rotator set at 100 rpm and incubated at 37° C. On each sampling day, the release medium was collected and replaced by 10 mL of fresh buffer. The collected release medium was tested for drug concentration using a microBCA Protein Assay Kit (obtained from Thermo Scientific, Pierce Protein Research Products). A final gel formulation that fulfilled the desired low initial burst and subsequent linear release profile was selected for in vivo analysis.

In Vivo Studies

Animal Care and Preparation

Male Wistar rats (Charles River Laboratories, Wilmington, Mass.) weighing 150-250 g were used and randomly assigned into 4 groups of 5 rats each. Rat groupings were as follows: Group 1 was the group with rats exposed to one week of gel treatment. Group 2 was the group with rats exposed to two weeks of gel treatment. Group 3 was the group with rats exposed to three weeks of gel treatment. Group 4 was the vehicle group. All rats were maintained on a standard laboratory diet and were initially allowed at least 3-4 days to acclimatize to the animal facility housing prior to the start of the study.

Gel Implantation

In an effort of minimizing suffering on the animals during gel implantation, the rodents were anesthetized with isoflurane (1.5% in oxygen), and ventilation was provided using a rodent ventilator. To minimize any unnecessary risk of infection, the injection sites (back of the rat) were shaved and swapped with 70% ethanol prior to injection. The desired CD-NP dose was 10-7 g/kg/minute (Soeki et al., *J. Am. Coll. Cardiol.*, 45:608-616 (2005)). 1.4 cc of freshly prepared gel were drawn into a 3 cc syringe, and a 20 G needle was then attached to the syringe tip. About 0.2 cc of gel was injected subcutaneously into each of the seven sites on the back of the rodent. After the injections, the rodents were returned back to the cage and allowed to recover. A second injection, which involved an exact procedural repeat of the first injection but on different sites, was carried out 48 hours later.

Blood Pressure Measurement

One of CD-NP properties for unloading of the heart is through veno-vasodilation. This results in a drop in blood pressure. As a non-invasive means of assessing the presence of circulating CD-NP released from the gel system, the rodent's blood pressure was measured at pre-determined time points and monitored over 18 days. Rodent blood pressure was measured using the CODA Non-invasive Blood Pressure System for Mice and Rats (Kent Scientific Corporation).

Plasma Evaluation

Treatment groups were sacrificed for blood collection at the respective sacrificial time points (i.e., 1 week, 2 weeks, and 3 weeks for plasma evaluation). Plasma analysis for the vehicle group was carried out at 3 weeks after injection. Radioimmumoassay (RIA) kits (obtained from Perkin Elmer Life Science) were used to evaluate plasma CD-NP and cGMP concentration (Del Ry S, *Clinical Chemistry and Laboratory Medicine*, 43:641-645 (2005)). The RIA assay was based on competition between $^{125}$I-peptide and CD-NPs binding onto a limited quantity of antibodies.

Urinary Output Evaluation 24 hours of urine were collected at four respective time points: baseline (before the start of study), after injection 1, after injection 2, and before the sacrificial time point. During the 24 hours of urine collection, individual rodents were placed into individual metabolic cages where urine was collected. Urinary volume was noted and tested for the presence of urinary CD-NP and cGMP.

Statistics Analysis

All data were expressed in mean±SEM. The comparison between each measurement was performed by t-test. Significant difference of $p<0.05$ was accepted.

Results

In Vitro Buffer Release

The nature of CD-NP polypeptides offered challenges for gel formulation development. CD-NP is a short chain molecule, making controlling its release difficult. After investigating the effects of different parameters on the CD-NP release profile, a gel formulation that mimics the desired low initial burst and subsequent zero order release profile was selected. The release profile for the selected gel formulation, presented in FIG. 1A, demonstrated a sustained CD-NP release for more than 30 days. It exhibited an initial burst of 11±1% of the total CD-NP loading. Thereafter, the rate of CD-NP release started to decrease and assumed a more linear release over the next 30 days. Up to 50±1% of the total CD-NP loading was released by day 31.

Based on the CD-NP concentration data collected at each time point, an estimate of the amount of CD-NP released on a daily basis was generated (FIG. 1B). Although the initial burst was relatively low, at 11±1%, this translated into 76±15.9 μg of CD-NP released. However, the burst effect was only observed within the first day. As soon as the "gel" was fully precipitated, CD-NP was released at a consistent level between 5.95 to 11.9 μg/day for the next 30 days.

To achieve a targeted dose of $10^{-7}$ g/kg/minute, the amount of gel required was quadrupled from 0.7 cc used in vitro to 2.8 cc. Bearing in mind the effects of the initial burst of the gel system, precaution was taken by separating the required 2.8 cc into 2×1.4 cc injections. Injections were carried out on Day 0 and on Day 2. This allowed a 48-hour recovery window in which the initial burst effect could dissipate.

The release profile of an injected gel is dependent on the kinetics of phase inversion as well on the rate of polymer matrix degradation. This, in turn, is dependent on intrinsic and extrinsic factors, one of which is the availability of water as the polymer matrix degrades hydrolytically. Studies have shown that in the subcutaneous environment, the relatively limited availability of water means that the polymer matrix tends to degrade at a slower rate as compared to that in vitro (Kim, *J. Pharm. Pharmacol.*, 54:897-905 (2002)).

Instead of injecting the entire 1.4 cc of gel into a single site, a total of seven multiple sites were injected with about 0.2 cc of gel each. It was hoped that given the larger surface area of the smaller gel, the polymer will degrade faster and hence achieve the desired release profile that most resembles the in vitro data.

In Vivo Studies

With one exception, all rats recovered well after each gel injection. Recovery typically took place within hours after injection. The death of the single rat, from the vehicle group, occurred after the second gel injection. Cause of death could be due to the series of events that the rat experienced following the first injection. Rats undergo multi-anesthetization on Day 0 and 2 during gel injection. In between the injections, the rats were subjected to multiple blood pressure measurements. Procedure for blood pressure measurement involved holding the rats in a confined space that is heated to 37° C. This series of events could have been too traumatic for the rat.

Blood Pressure Measurement

Figure 2:
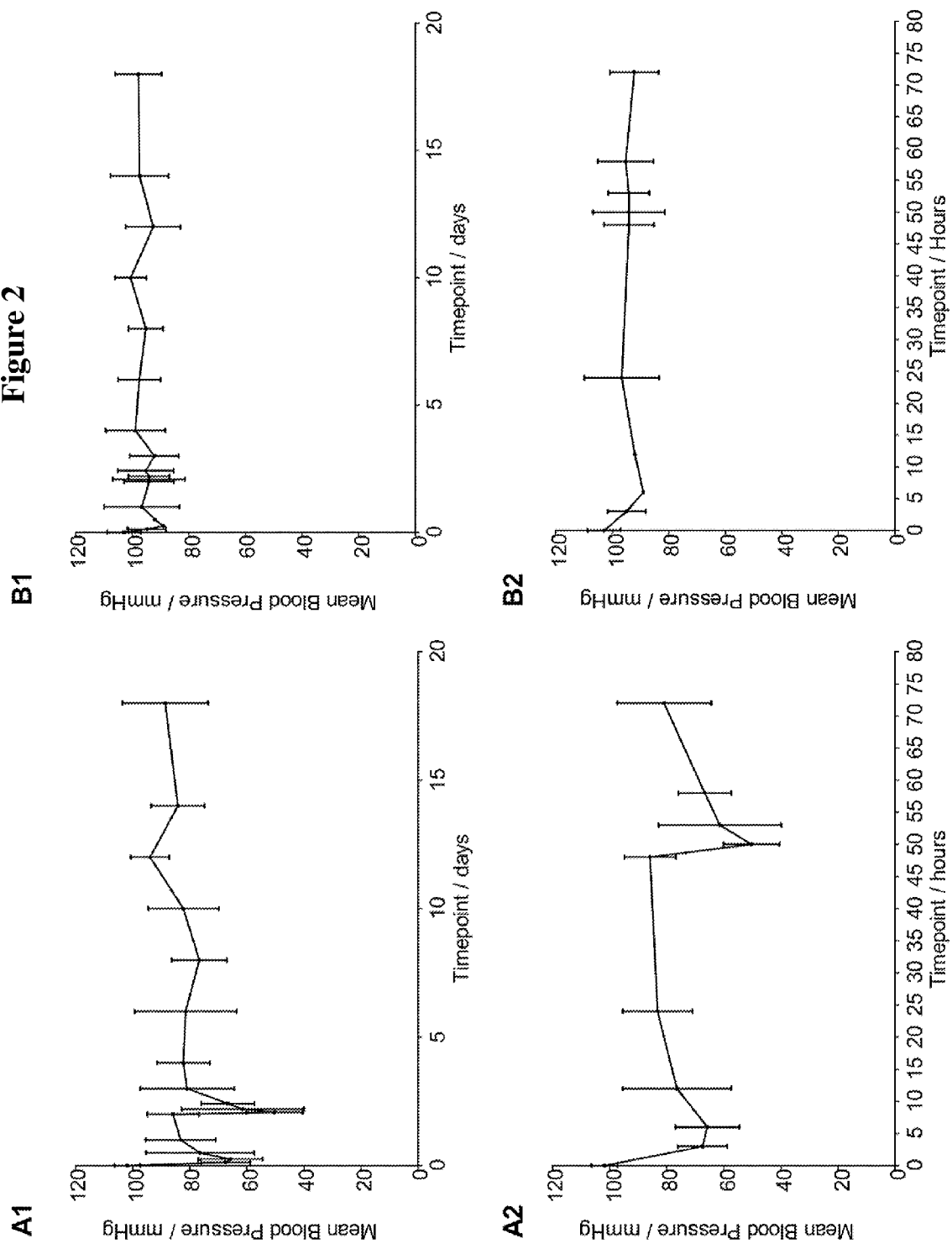

As a non-invasive way of assessing the presence of circulating CD-NP levels in the rodents, blood pressure was measured. Given the veno-dilating property of CD-NP, any presence of circulating CD-NP will be indicated by a lower blood pressure. As such, the blood pressure (BP) was monitored for both the treatment and vehicle group. BP measurements were taken once every 2-3 days with more readings taken within 24 hours after each injection. FIGS. 2A1 and 2B1 show the mean BP trend measured over 18 days of the study for the treatment and vehicle groups, respectively. FIGS. 2A2 and 2B2 show the mean BP trend, magnified over the initial 3 days.

The BP trend for the vehicle group exhibited a more consistent mean BP of between 89.0 to 100.6 mmHg throughout the study duration. There were, however, some drops in BP observed during the first 3 days of the study, which was mostly likely due to the repeated exposure to isoflurane during the anesthetization process.

As expected, the mean BP for the CDNP-treated groups dropped from 102±1.2 mmHg to 66±1.7 mmHg within the first six hours after the first gel injection. This drop coincided with the initial burst release from the gel system. The BP recovered to about 83±1.8 mmHg within the first 24 hours. Following the second injection on Day 2, the BP dropped from 86±1.1 mmHg to 50±3.0 mmHg. After the BP recovery from the initial burst effect of the second injection, the mean BP was maintained between 76.7 mmHg to 90.9 mmHg until the end of the 18th day. This lowered BP was significant as compared to the vehicle. The BP trend from the CDNP-treated group was confirmation that CD-NP was constantly being released from the gel system over the entire 18 days and was exerting its bioactive function of vaso-dilation.

Plasma Concentrations

Figure 3:
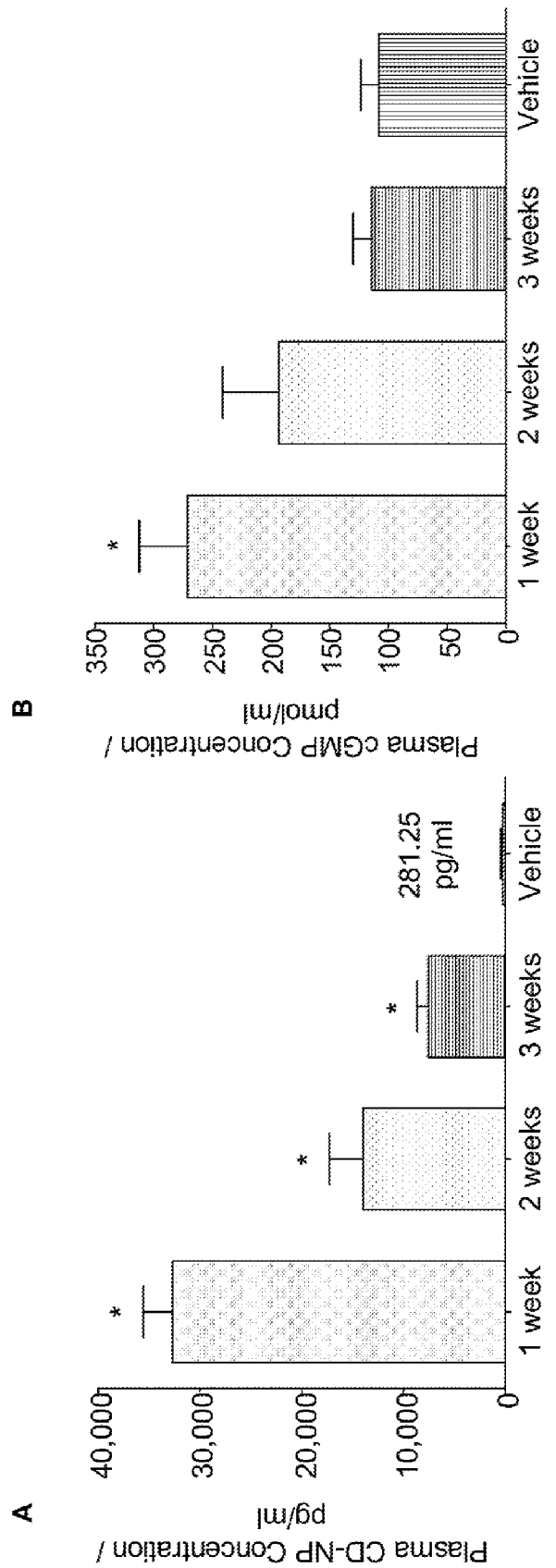
FIG. 3A is a bar graph plotting plasma CD-NP concentrations for the vehicle group and at week 1, week 2, and week 3 for the treatment group.
FIG. 3B is a bar graph plotting plasma cGMP concentrations for the vehicle group and for the treatment group at week 1, week 2, and week 3. * represents P<0.05 between the treatment group and vehicle group.

Plasma CD-NP (pCD-NP) concentrations were quantified using radioimmunoassay (RIA) kits. Results of the pCD-NP concentration measurements demonstrated a sustained release of CD-NP over the three week study duration (FIG. 3A). Measured pCD-NP concentrations were 33,000±2888 pg/mL, 14,000±3302 pg/mL, and 8,000±1115 pg/mL at one, two, and three weeks, respectively. pCD-NP concentrations measured from the vehicle group were found to be around 280±160.4 pg/mL. The results from the CDNP-treated groups demonstrated an elevated pCD-NP level that was significantly different from the vehicle group.

If the in vitro data was representative of in vivo release, the one would expect the pCD-NP concentrations for the week 3 time point to be similar to that of week 2. However, this was not the case. There were two possibilities for this. Firstly, it could be due to the difference in rate of polymeric degradation of the polymer matrix in vivo as compared to in vitro. A second possibility was a loss of CD-NP bioactivity. PLGA polymer degrades through hydrolysis, which is highly dependent on pH and the availability of water. In the in vitro setting, the injected gels were surrounded by buffer medium, which were constantly being replaced with fresh buffer during each sampling time point. On the other hand, there was generally less availability of water in the subcutaneous tissue for uptake into the injected gel. As such, the degradation rate for the in vivo gels might be relatively slower. This may account for the slower release and hence the lowered CD-NP release over the 3 time points.

Another possible explanation for the decrease in measured pCD-NP could be due to the degradation of CD-NP. As PLGA matrix degrades into lactic and glycolic acids, it created pockets of slightly acidic environment in the polymer matrix (Kim, *J. Pharm. Pharmacol.*, 54:897-905 (2002)). This internal acidic environment might degrade the CD-NP polypeptide. Since the RIA kit only works well in detecting intact CD-NP, the resulting pCD-NP concentrations could be lower than expected.

To test for the bioactivity of the released CD-NP, plasma cyclic guanosine 3'5' monophosphate (pcGMP) concentrations were measured. cGMP is a secondary messenger activated through the binding action of CD-NP onto NPR-A/B receptors. It was shown that only an intact ring structure activates NPR-A receptor (Dickey et al., *J. Biol. Chem.*, 283: 35003-35009 (2008) and Misono et al., *Biochem. Biophys. Res. Comm.*, 123:444-451 (1984)). Hence, the presence of cGMP would confirm the biological activity of released CD-NP. The pcGMP concentrations were measured to be 270±41.4 pmol/mL, 190±48.1 pmol/mL, and 114±15.8 pmol/mL at the respective one, two, and three week time points. pcGMP concentrations from the vehicle group revealed a concentration of about 108±15.5 pmol/mL (FIG. 3B). Although pcGMP concentrations were significantly elevated at week 1 as compared to vehicle, there was a less significant difference for week 2 and 3 measurements when compared to the vehicle.

The plasma cGMP concentrations are dependent on the amount of pCD-NP and availability of NPR-A/B receptors. Studies demonstrated that CD-NP activation of cGMP is dose-dependent, and this relationship plateaus at high CD-NP concentrations (Lisy et al., *J. Am. College Card.*, 52:60-68 (2008) and Dickey et al., *J. Biol. Chem.*, 283:35003-35009 (2008)). The maximum pcGMP concentrations in this particular rodent species were between 250 pmol/mL to 300 pmol/mL. Given the high level of pCD-NP administered, one would expect maximum activation of cGMP throughout the three weeks duration. This, however, was not observed.

There was one possible explanation for this observation. In this study, the objective was to achieve a sustained release effect of CD-NP from the gel system. As such, an excess of CD-NP was loaded into the depot. This meant that, as discussed herein, a high level of pCD-NP in plasma was achieved even at three weeks. The abundant availability of pCD-NP led to continual maximum activation of cGMP over an extended duration. This high cGMP activation rate might not be perceived by the body as 'normal'. As such, compensatory responses might intervene to regulate this abnormally high amount of pcGMP. There are several possible compensatory responses. Within the natriuretic peptide pathway, there might be a partial down regulation of NPR-A/B receptors. This prevents further binding of CD-NP onto the receptor. NPR-C receptors, also known as the NPs clearance receptor, could go into over-drive, increasing the degradation of CD-NP. These responses will reduce the rate of cGMP activation. A second mechanism for the decreased in plasma cGMP may be in part due to increased cGMP excretion via the kidneys as supported by the increased urinary cGMP excretion. A third mechanism may be due to the degradation of cGMP by phosphodiesterases (PDE) such as PDE V.

Urinary Output Evaluation
Urinary Output Volume

The 24-hour urinary outputs for both the treated and vehicle rodent were measured (Table 1). Mean 24-hour baseline urine outputs for the treated and vehicle group were 15±1.3 mL and 13±0.9 mL, respectively. After the first and second gel injection for the treatment group, the mean urinary output increased to 32±2.5 mL and 32±1.8 mL, respectively. The increase in urinary volume output was about twice that of the baseline volume. CD-NP was also known to be diuretic ((Lisy et al., *J. Am. College Card.*, 52:60-68 (2008) and Dickey et al., *J. Biol. Chem.*, 283:35003-35009 (2008)). As such, the increase in the urinary output right after the injections was related to the amount of CD-NP administered during the first 24 hours after each injection. This was further evidence suggesting that CD-NP released from the gel polymer matrix was biologically active.

TABLE 1

24 hour urinary output volume for baseline, first and second post-injections, and prior to sacrifice.

| Time point | Treatment Group (mL) | Vehicle Group (mL) |
| --- | --- | --- |
| Baseline | 15 | 13 |
| After Injection 1 | 32.4 | — |
| After injection 2 | 31.5 | — |
| 1 week | 11.9 | — |
| 2 weeks | 14 | — |
| 3 weeks | 12.5 | 11.9 |

Urinary CD-NP and cGMP

Figure 4:
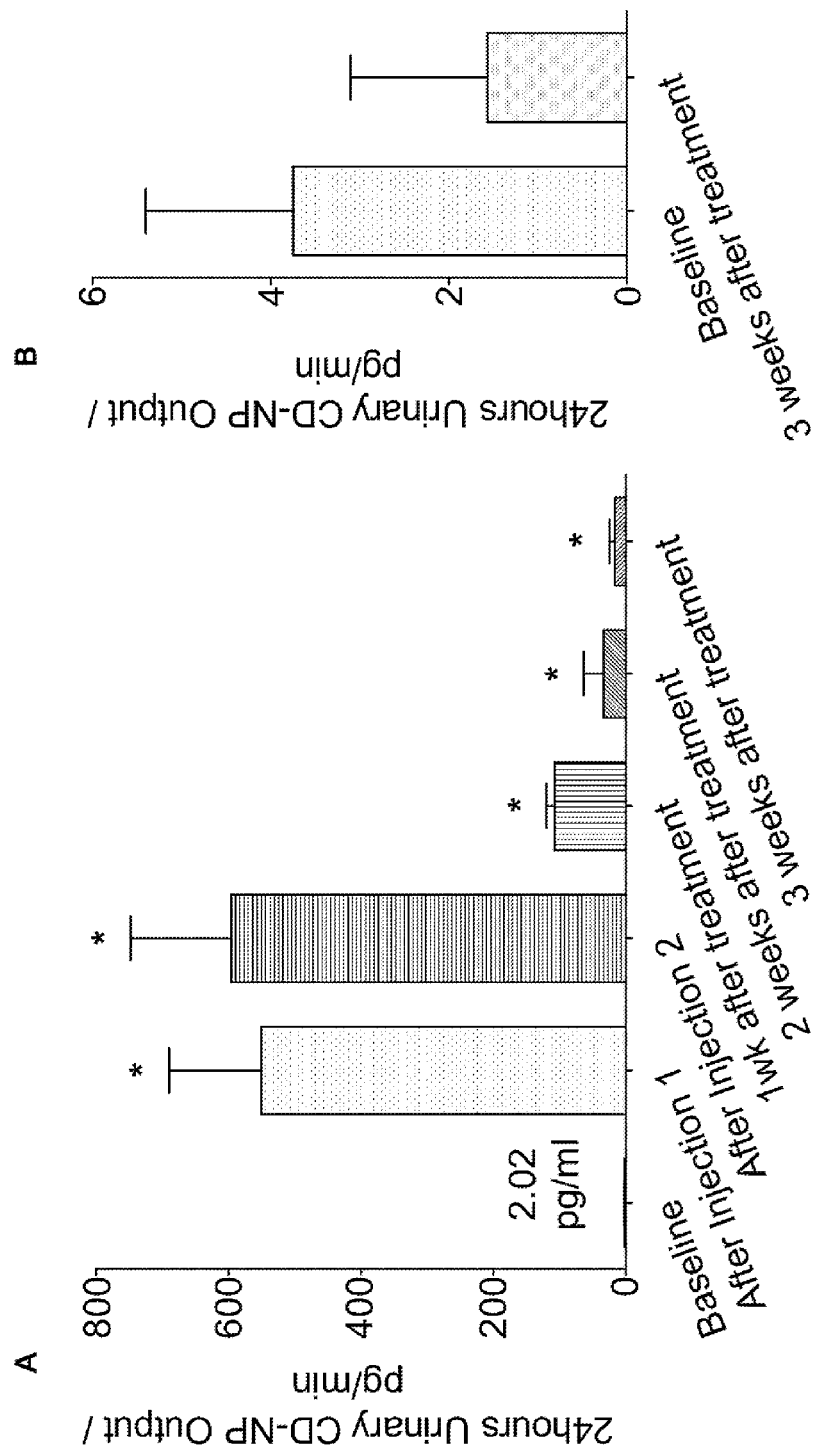
FIGS. 4A and 4B are graphs plotting the 24-hour urinary CD-NP output for the treatment group (A) and vehicle group (B). * represents P<0.05 between the treatment group and vehicle group.

Background urinary CD-NP (uCD-NP) levels were measured at 2±0.10 pg/minute and 4±1.65 pg/minute for treatment and vehicle groups, respectively (FIGS. 4A and 4B). For the treatment group, the uCD-NP levels were measured at 550±139.60 pg/minute and 600±151.90 pg/minute after the first and second injections, respectively. Immediately after the gel injections, there was a burst release of CD-NP from the gel. Most of this un-used CD-NP was excreted out of the system through urinary excretion. This accounted for the high uCD-NP output. The amount of CD-NP excreted at one, two, and three weeks reduced to 107±12.70 pg/minute, 34±29.72 pg/minute, and 17±8.19 pg/minute, respectively. These were statistically significant when compared with the baseline level. As mentioned, following the burst release, the amount of CD-NP released from the gel system reduced to a more sustainable level. This, in turn, led to the lower uCD-NP output observed. There was no significant difference in uCD-NP output observed between the baseline and 3 weeks urinary output for the vehicle group.

Figure 5:
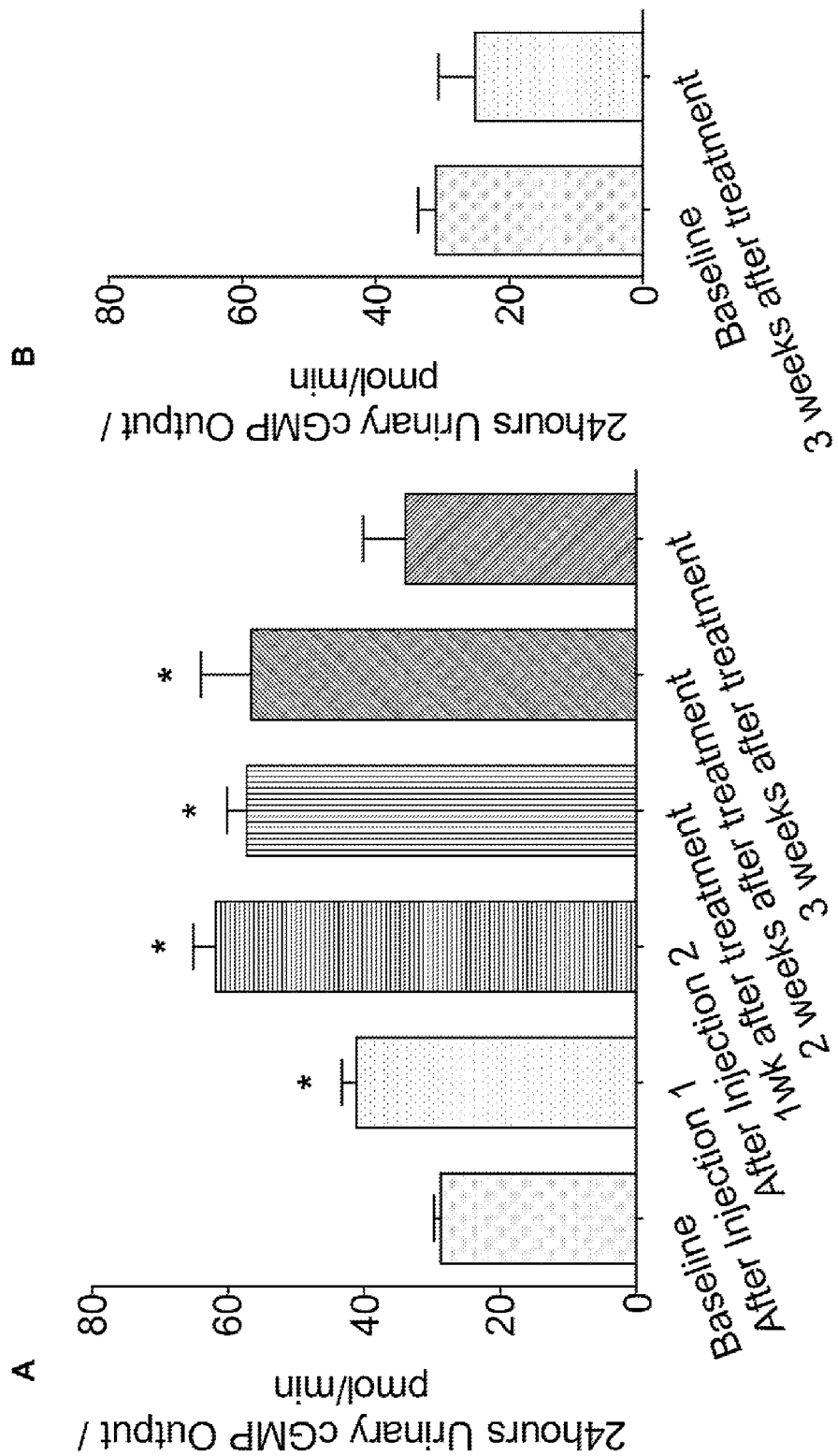
FIGS. 5A and 5B are graphs plotting the 24-hour urinary cGMP output for the treatment group (A) and vehicle group (B). * represents P<0.05 between the treatment group and vehicle group.

Baseline urinary cGMP (ucGMP) levels were measured at 29±0.10 pmol/minute and 31±2.68 pmol/minute for treatment and vehicle group, respectively (FIGS. 5A and 5B). There were no significant changes in the ucGMP output for the vehicle group at three weeks after the injection of the blank gel. As for the treatment groups, ucGMP output was significantly increased following gel injections. ucGMP output was 41±2.16 pmol/minute and 62±3.32 pmol/minute after the first and second injections, respectively. The ucGMP output after the first injection was slightly lower than that measured for the second injection. This was probably due to the fact that there was a lapse time between CD-NP diffusing out of the gel system into the blood, binding of CD-NP with NPR-A/B receptors, and the activation of cGMP to the filtration of pcGMP in the kidney. ucGMP output continued to remain high at one and two weeks. It, however, dropped to a level that was not significant at three weeks after the treatment. One interesting observation was that the ucGMP output level was consistently high at week 1 and 2.

These results demonstrate the effects on blood pressure, plasma CD-NP, plasma cGMP, urinary CD-NP, and urinary cGMP. These results also demonstrate an elevated pCD-NP level throughout the three week treatment duration. The high level of recorded uCD-NP was consistent with the elevated pCD-NP. Bioactivity of released CD-NP was also proven to be retained, as seen by the initial elevation of pcGMP level at week 1, and by the sustained hypotensive state of the treated rats.

Over longer times, however, pcGMP level did not sustain the saturation level that was predicted by the level of pCDNP. Following pcGMP saturation level at week 1, pcGMP gradually decreased over the next 2 weeks to a level that was not significantly different from the baseline level. Evidence from ucGMP excretion suggested that this decrease in pcGMP was not due to the loss of bioactivity of released CD-NP. Despite the decreasing pcGMP level from week 1 to week 3, a constant high level of ucGMP was recorded up to 2 weeks into treatment. Instead, it was believed that following the initial days of saturation level of cGMP production, the body perceived the level as 'abnormal.' As such, compensatory responses could have intervened to regulate this abnormally high level of circulating pcGMP. The compensatory responses were believed to be of two types, both of which help reduce circulating pcGMP.

The first mechanism could work by reducing the high cGMP activation rate. Within the NP/cGMP pathway, there could be down regulation of NPR-A/B receptors, thus reducing cGMP production. NPR-C receptor might also be 'set' into over-drive mode to remove rapidly circulating CD-NP. This could aid in reducing the pCD-NP concentration and in turn, reduce the availability of CD-NP for binding onto NPR-A/B receptors. This increased pCD-NP clearance was confirmed by the elevated uCD-NP output. Outside of the NP/cGMP pathway, there was another cGMP pathway known as NO-sGC/cGMP pathway. This pathway also promotes cGMP production and could also be down regulated to further reduce cGMP production.

The second mechanism could be aimed at reducing the circulating pcGMP level. This could be achieved by increasing cGMP removal rate through degradation of cGMP by phosphodiesterases or more directly through urinary excretion.

Based on the high level of sustained ucGMP output that was recorded, the dominant reason for the gradual drop in pcGMP level from week 1 to week 3 was due to the high removal rate via urinary excretion.

Example 3

Natriuretic Polypeptide Release Properties

In vitro studies were performed to determine the release properties of CU-NP polypeptides from polymer gels. An injectable gel system was designed and used to evaluate sustained release of CU-NP polypeptides over one month. Several gel parameters were investigated. First, three types of polymers were investigated: PLGA (50/50) with an intrinsic viscosity 0.4 dL/g (IV0.4), PLGA (50/50) with an intrinsic viscosity of 0.2 dL/g (IV0.2), and acid-capped PLGA (50/50) with an intrinsic viscosity of 0.2 dL/g (IV0.2A). Second, three different percentages of polymer within the gel preparation were investigated: 20 percent polymer (PGLA), 30 percent polymer (PGLA), and 40 percent polymer (PGLA). Third, different levels of triacetin solvent were evaluated: zero percent triacetin, 10 percent triacetin, and 20 percent triacetin. Fourth, two drug loading concentrations were tested: 0.15 percent CU-NP polypeptides and 0.3 percent CU-NP polypeptides. All gels were dissolved in NMP unless otherwise stated. Percentages were calculated based on w/w ratio.

Initial drug burst release depended on the type of polymer employed in the gel system. In this study, polymers of different intrinsic viscosity were used to investigate on the effects of polymer molecular weight on the initial release profile. Intrinsic viscosity (IV) was related to the molecular weight (Mw) of the polymer. The higher the IV, the higher was the molecular weight of the polymer.

Figure 6:
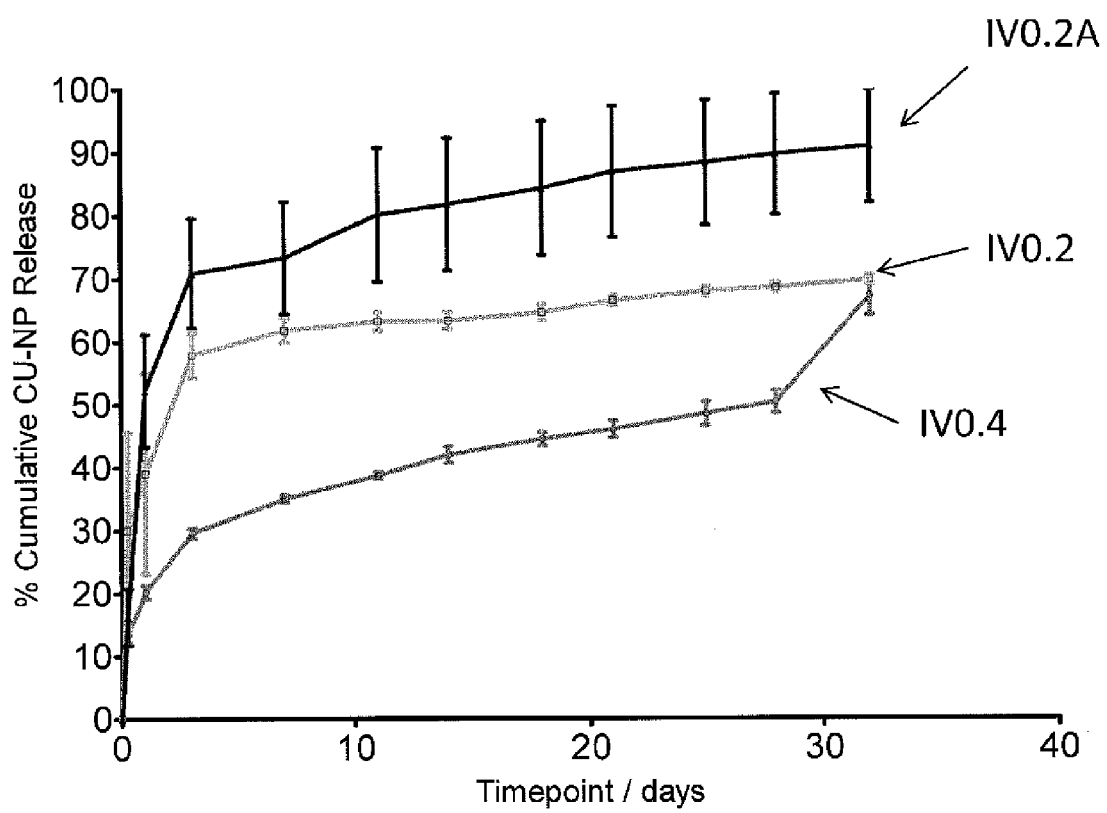
FIG. 6 is a graph plotting the effect of polymer type on the percent of cumulative CU-NP release in vitro.

Gel systems with a higher Mw exhibited a lower initial drug burst (FIG. 6). IV0.2A referred to a polymer chain that was capped at the end terminal with an acid group. As the end terminal does not play a role in determining the initial drug release, both initial drug release from IV0.2 and IV0.2A system were expected to be similar. As expected, both the IV0.2 and IV0.2A system exhibited similar initial CU-NP burst release. The acid-capped terminal system, however, exhibited an increased rate of polymeric degradation. This translated into a faster subsequent rate of drug release (FIG. 6).

Figure 7:
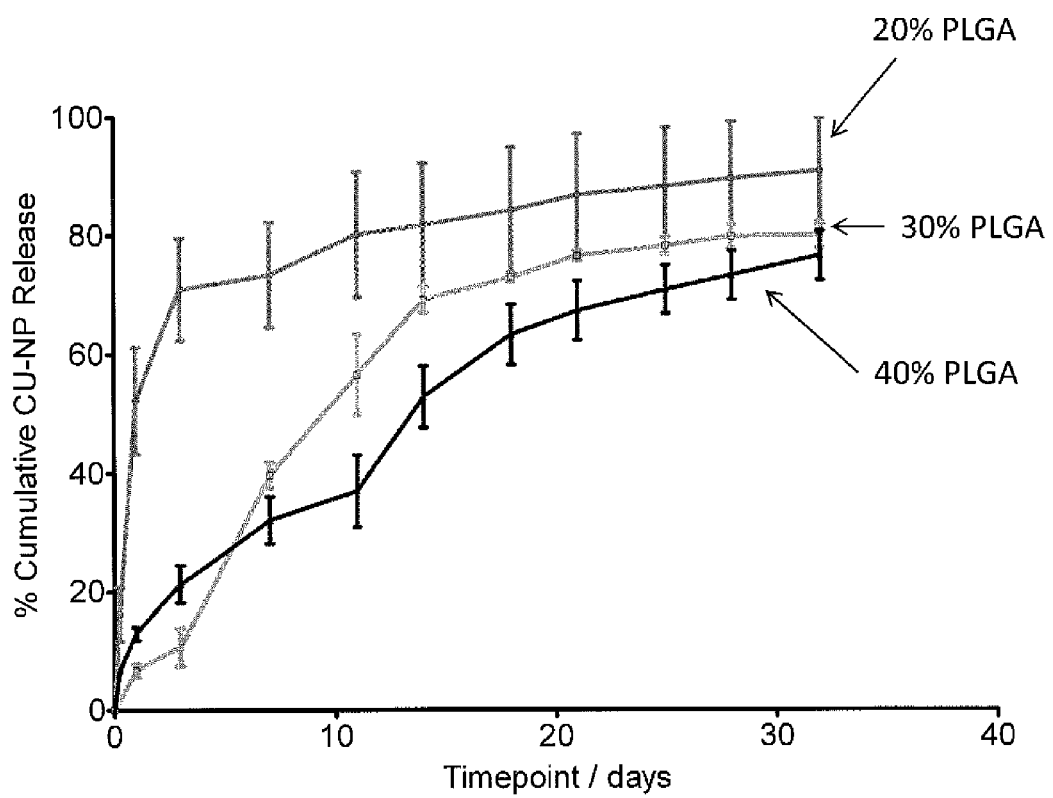
FIG. 7 is a graph plotting the effect of polymer concentration on the percent of cumulative CU-NP release in vitro.

Different polymer concentrations were used to investigate the effects of polymer concentration on initial burst release. Gel systems with a higher polymer concentration were more viscous and can exhibit a slower phase separation or gelation rate, increasing the diffusion barrier with the formation of a thicker and denser outer polymeric shell (FIG. 7). In addition, a reduction in the initial burst release was observed with higher polymer concentrations (FIG. 7).

FIG. 7 also revealed that 30% PLGA exhibited a lower burst release as compared to 40% PLGA system. This difference was due to the shape of the gel formed during the initial injection. Shape and size of the injected gel were involved in controlling the initial burst too. Changes in shape and size of the gel affected the amount of exposed surface areas and hence, increase or decrease the amount of drug release.

In situ polymer precipitation system can function on the principle of solvent-water exchange. Upon injection into buffer solution, solvent from within the gel solution can efflux out of the system, while water from the surrounding can influx into the gel. This solvent-water exchange process can result in the precipitation of the hydrophobic polymer.

The rate of solvent-water exchange can contribute to the porosity of the shell layer. Generally, a hydrophilic solvent such as NMP tends to efflux out of the gel system rapidly, forming huge interconnected pores within the shell layer. These polymer-lean pores allow drug to diffuse easily out of the gel system and can result in a high initial burst release. When a hydrophobic solvent such as triacetin is used, it tends to stay in the gel solution longer resulting in a slower solvent efflux and slower water influx. This leads to a slower rate of polymer precipitation, which tends to form denser and smaller non-interconnected pores. This polymer-rich shell layer can retard drug diffusion and can reduce the initial drug release.

Figure 8:
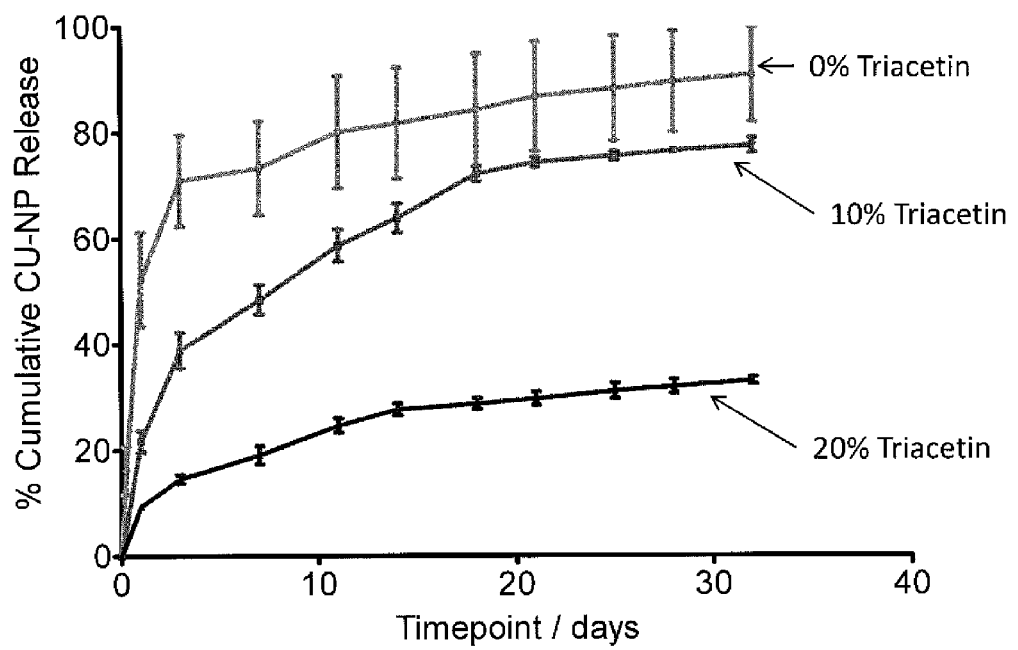
FIG. 8 is a graph plotting the effect of solvent (triacetin) concentration on the percent of cumulative CU-NP release in vitro.

The rate of solvent-water exchange can be modified by changing the solvent content within the gel system. Different co-solvent concentrations were used to investigate the effects of co-solvent on initial burst release. Increasing the amount of the hydrophobic solvent in the system altered the rate of solvent-water exchange and changed the shell layer morphology (FIG. 8).

Figure 9:
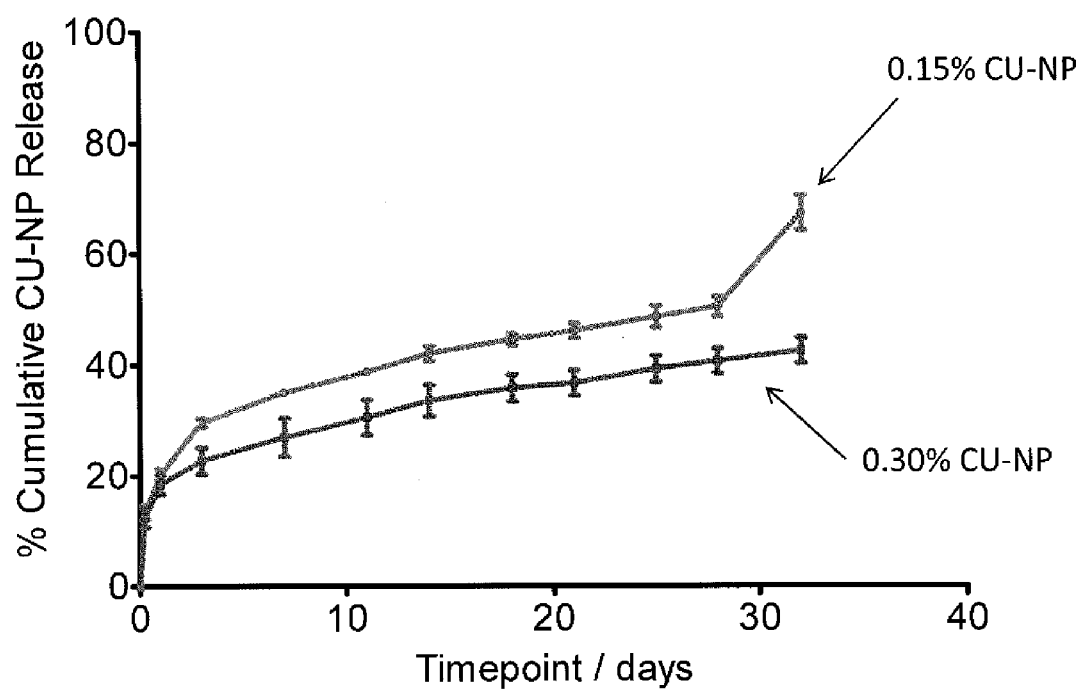
FIG. 9 is a graph plotting the effect of CU-NP concentration on the percent of cumulative CU-NP release in vitro.

The CU-NP release profiles from two gel system with different drug loading amounts (0.15 and 0.30 percent) were assessed (FIG. 9). Both loading amounts exhibited release profiles with similar initial burst release. Since both gel formulations were similar, the release profiles should be the same. In this case, the only difference was in term of the absolute amount of drug that was released.

Figure 10:
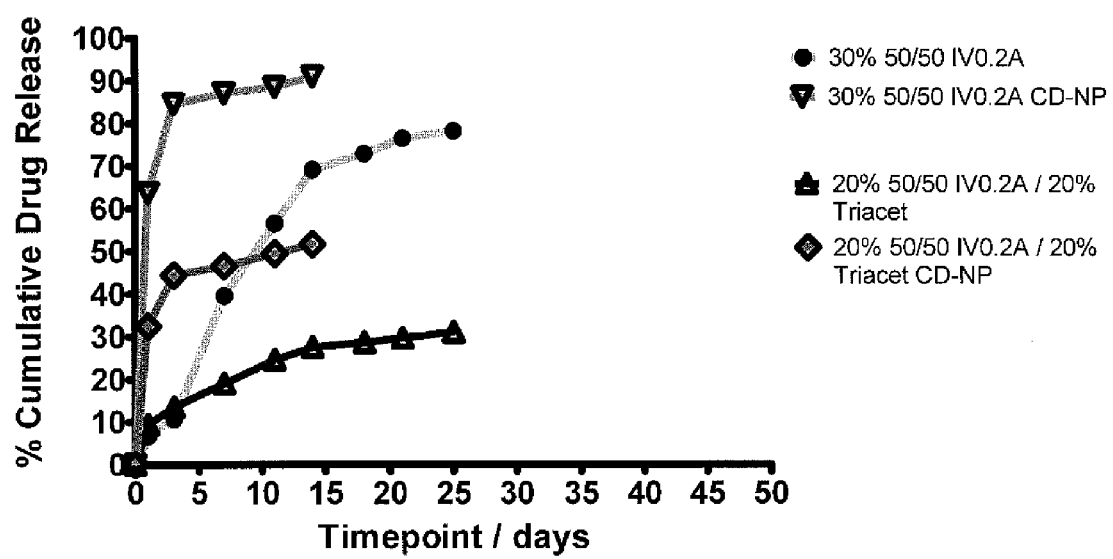
FIG. 10 is a graph plotting comparing the release rates of CD-NP as the percent of cumulative drug release in vitro.

FIG. 10 shows the release profile of CD-NP. In addition, it appeared that CD-NP polypeptides were being released from the system at a much faster rate as compared to that of CU-NP polypeptide. This difference in rate of drug release could be due to drug hydrophilicity and solvent solubility.

Example 4

In Vivo Evaluation of an In Situ Polymer Precipitation Delivery System Using An Acute Myocardial Infarction Rat Model Materials Poly (D,L-lactic-co-glycolic acid) (PLGA) (17 kDa, 50:50 dl-LA to GA ratio, inherent viscosity: 0.2 dL/g) from Purac Biomaterials, Gorinchem Netherlands, was used in the gel formulations. HPLC grade N-methyl-2-pyrrolidinone (NMP) and triacetin, purchased from Sigma Aldrich and Fisher Scientific, respectively, were used as solvents. Both solvents were of low toxicity. CD-NP polypeptide was supplied by Nile Therapeutics, Inc.

Synthesis of In Situ Polymer Precipitation Delivery System

Injectable gel formulation preparation was as follows. Briefly, CD-NP was dissolved in NMP solvent, and the resulting suspension was allowed to stir for at least 3 to 4 hours before the addition of pre-weighed polymer and triacetin solution. The quantities added were such that the polymer and triacetin content was 40% and 20% by weight, respectively, with the CD-NP being present at 0.45% w/w. The final solution was allowed to homogenize overnight. Fresh gel samples were prepared 1 day in advance for each injection.

Animal Care and Preparation

Male wistar rats (Charles River Laboratories, Wilmington, Mass.), weight of 150-250 g, were used and randomly assigned into two groups of 15 rats each. Rat groupings were as follows: Group 1—Vehicle Group (Gel only); and 2—Treatment Group (Gel and CD-NP). All rats were maintained on a standard laboratory diet and were initially allowed at least 3 to 4 days to acclimate to the animal facility housing prior to the start of the study. Group population of 15 rats each was chosen to take into account the possibility of mortality sustained from model creation surgical and/or unsuccessful model creation. For the study protocol, all rats were injected with 1.0 mL of gel solution at day 0 followed by model creation surgical procedure on day 1 and finally a second 1.0 mL injection on day 3. Rats were sacrificed at week 3 for data collection.

Gel Implantation

In an effort of minimizing suffering on the animals during gel implantation, the rodents were anesthetized with isoflurane (1.5% in oxygen), and ventilation was provided using a rodent ventilator. To mitigate any unnecessary risk of infection, the injection sites (back of the rat) were shaved and swapped with 70% ethanol prior to injection. The desired CD-NP dose was $10^{-7}$ g/kg/minute. 1.0 cc of freshly prepared gel was drawn into a 3 cc syringe, and a 20 G needle was then attached to the syringe tip. About 0.2 cc of gel was injected subcutaneously into each of the five sites on the back of the rodent. After the injection, the rodents were returned back to the cage and allowed to recover. A second injection, an exact procedural repeat of the first injection and on different sites, was carried out 72 hours later.

Acute Myocardial Infarction Model Creation

Rats were anesthetized. Chest hair was shaved, and the shaved area was swapped with 70% ethanol prior to chest dissection. The chest was opened using an intercostals incision and retracted with a rat rib retractor. The left auricle was slightly retracted to expose the entire left main artery system. Ligation, aided with a tapered forceps, was carried out by tying using a 7-0 suture on the anterior descending coronary artery (LAD). The immediately vicinity beneath the ligation was observed briefly to confirm the presence of ischemia. A dose of lidocaine was administered over the heart to reactivate the heart rhythm. The chest wall was then closed with a 5-0 Ticron blue polyester fiber suture with one layer through the chest wall and muscle. To minimize any inflammation, before the suturing of the second layer through the skin, several drops of hydrogen peroxide were added. The rats were removed from the ventilator and kept warm over a heating pad. 0.07 cc of Buprenex was injected into the blood vessel to aid the recovery process.

Blood Pressure Measurement

As a non-invasive means of assessing the presence of circulating CD-NP released from the gel system, rodents' blood pressure was measured at pre-determined time points (i.e. before start of study, after injection 1 and 2, and before acute study). Rodents' blood pressure was measured using the CODA Non-invasive Blood Pressure System for Mice and Rats from Kent Scientific Corporation.

Echocardiography Studies

Echocardiography was performed within 7 days before the scheduled acute study. Echocardiography was performed using a Vivid 7 system (GE Healthcare, Milwaukee, Wis.) equipped with a 10S ultrasound probe (11.5 MHz) with ECG monitoring. Briefly, chest hair was shaved, and ultrasonic scans were performed on all rats in supine position. M-mode image and gray scale 2D images (300-350 frames/sec) of parasternal long axis and mid-LV were recorded for off-line analysis. End-systolic (ESV), end-diastolic and stroke volumes (SV), and ejection fraction (EF) were calculated using the Teichholz formula. All parameters represented the average of 3 beats.

Acute Study

Acute study was performed 3 weeks post MI. Prior to the acute study, rat weight was collected for heart/body weight analysis. Rats were anesthetized. A PE-50 tubing was inserted into the carotid artery for blood sampling. Blood for CD-NP and cGMP analysis was collected in heparin or EDTA tubes on ice. After centrifugation at 2,500 rpm at 4° C. for 10 minutes, plasma was aliquot and stored at −80° C. until assay. After confirming that the rat was clinically dead, the rib cage was opened, and the heart was harvested for heart tissue analysis. Observations were made to confirm the presence and degree of myocardial infractions. Heart weight was measured before the dissection of the heart for left ventricle (LV) harvesting. Sectioned LVs were immersed in formalin for histological analysis. Picrosirius red staining was utilized to assess collagen content. An Axioplan II KS 400 microscope (Carl Zeiss, Inc., Germany) and KS 400 software were utilized to analyze the histological slides and to calculate the percentage of picrosirius red stain.

Plasma Evaluation

Radio-immumo Assay (RIA) Kit obtained from Perkin Elmer Life Science was used to evaluate plasma CD-NP and cGMP concentration. The RIA assay involved competition between $^{125}$I-peptide and CD-NPs binding onto a limited quantity of antibodies. RIA was capable at detecting both native CNP and designer CD-NP.

Urinary Output Evaluation 24 hours of urine were collected on 2 time points: baseline (before the start of study) and before sacrificial time point. During the 24 hour urine collection, individual rodents were placed into individual metabolic cages where urine was collected. Urinary volume was noted and tested for the presence of urinary CD-NP and cGMP.

Statistical Analysis

All data were expressed in mean±SEM. The comparison between each measurement was performed by t-test. Significant difference of $p<0.05$ was accepted.

Results

A total of 30 rats were used in the study. However, 4 rats from each group did not survive the ligation surgery of MI creation. Deaths resulted from punctured heart during LAD ligation, massive internal bleeding, or related surgical procedure. Other than the recorded deaths, one rat from the treatment group (Gel+CD-NP) and three rats from the vehicle group (Gel only) were also excluded from data computation due to poorly defined-infarction or unsuccessful MI creation. No death was recorded as a result of gel injection. In all, statistical data discussed was based on 8 and 10 rats from vehicle and treatment groups, respectively.

Blood Pressure Measurement

Given that CD-NP exhibits venodilating property, any presence of circulating CD-NP is evident from lowered blood pressure (BP). In this AMI model rat study, BP was measured before the start of the study and before rat sacrifice. For additional data collection, BP also was monitored immediately after each injection for analysis of BP drop as a direct result of the gel initial burst release.

Figure 11:
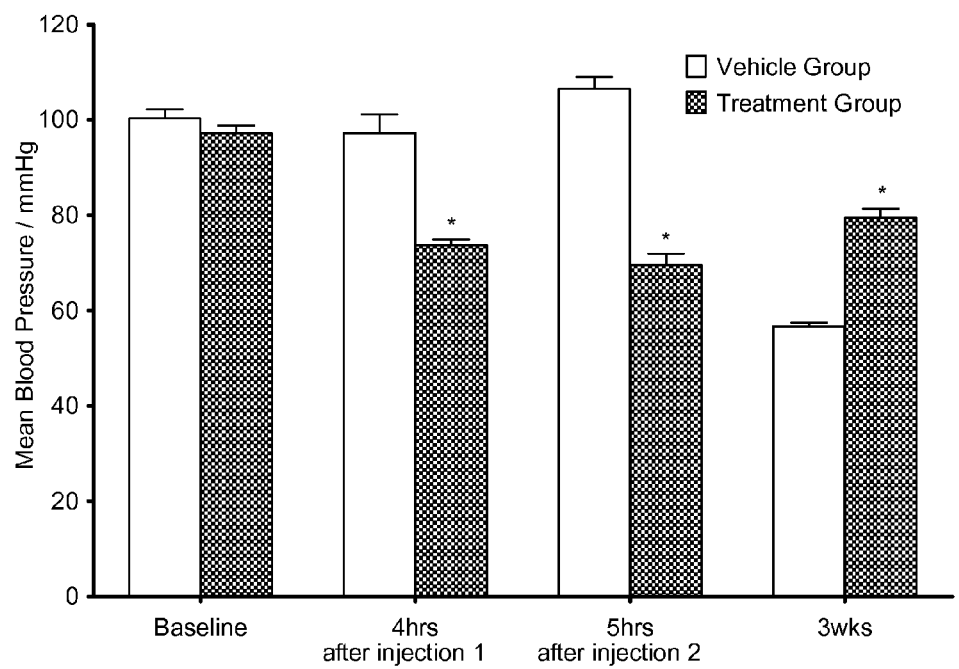
FIG. 11. Blood pressure measurement at pre-determined time points. *P<0.05, Treatment vs. Vehicle of similar time point.

FIG. 11 represent BP data collected at the pre-determined time points. No BP change was observed in vehicle group following the two gel injections. However, at 3-week time point, BP dropped from 100±1.9 mmHg to 56.6±0.8 mmHg. As for treatment group, BP dropped to 73±1.1 mmHg and 69±2.3 mmHg following the 1st and 2nd gel injections, respectively. BP at 3-week was observed to be 79±2.0 mmHg.

Three observations were made from BP measurements. Firstly, in this study, BP of treatment group were 73±1.1 mmHg and 69±2.3 mmHg following the 1st and 2nd gel injections, respectively. Compared to a predicate study (Lim et al., *J. Cardiac Failure*, 18:S63 (2012)) where BP of treatment group was observed to drop to 66±1.7 mmHg and 50±3.0 mmHg after first two injections, the drop in BP for the current study after the 1st and 2nd injection was less drastic. Observations of rat activity level post injection suggest that the rodents accepted this dropped in BP better than the more drastic dropped in the predicate study. This difference in BP drop was due to the drug dosage given in this study (1.0 cc per injection), which was lower than in the predicate study (1.4 cc per injection). Initial drug burst release was observed from the gel system, and this sudden elevation in plasma CD-NP resulted in blood BP drop. The reduction in initial burst amount of drug (partly due to lower loading) resulted in a more acceptable BP drop.

Secondly, BP at 3-week for treatment group was measured to be 79±2.0 mmHg. This lower BP level as compared to baseline suggested that the gel was eluting biologically active CD-NP even at 3 weeks.

Thirdly, BP in the vehicle group remained unchanged following the two injections. However, as the infarction spreads and worsens, heart function decreased drastically leading to a drop in BP from 100±1.9 mmHg to 56.6±0.8 mmHg at 3 weeks. Interestingly, the BP of treatment group of the same time point did not experience that extensive a drop in BP. Instead, BP hovered at 79±2.0 mmHg, further demonstrating attenuation of the infarction effects in CD-NP treated group.

Plasma Concentrations

Figure 12:
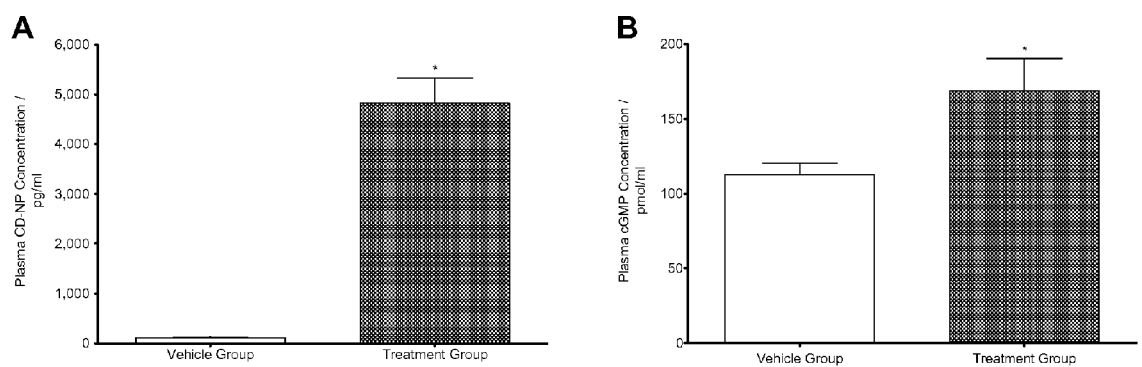
FIG. 12A is a graph plotting plasma CD-NP concentration at 3-weeks.
FIG. 12B is a graph plotting plasma cGMP concentration at 3-weeks. *P<0.05, Treatment vs. Vehicle.

Plasma CD-NP concentration (pCD-NP conc.) and cGMP concentration (pcGMP conc.) were quantified using the Radio-immumo Assay (RIA) Kit. Data collected was represented in FIG. 12. pCD-NP conc. in vehicle group was found to be 120±6.2 pg/mL, while that of treatment group was significantly elevated to 5,000±505 pg/mL at 3 weeks.

pCD-NP measured from this rat study concured with data collected from the predicate study. In the previous study, 2.8 cc of gel administered yielded 8,000±1115 pg/mL pCD-NP conc. at 3 weeks. This approximately translates into 2800 pg/mL per 1 cc of gel administered. In this study, 2.0 cc of injected gel yielded a pCD-NP conc. of 5,000±505 pg/mL. This approximately translates into 2500 pg/mL per 1 cc of gel administered. This affirmed that the gel release was consistent between the two studies.

To test for the bioactivity of released CD-NP, pcGMP conc. was measured. cGMP is a secondary messenger activated through the binding action of CD-NP onto NPR-A/B receptors. Thus, the presence of cGMP confirms functionality of released CD-NP. From FIG. 12, pcGMP conc. in vehicle group was found to be 112±8.0 pmol/mL. This collated well with baseline pcGMP conc. in normal rats of 108±15.5 pmol/mL. Treatment group, on the other hand, reflected a significantly elevated pcGMP conc. of 170±21.4 pmol/mL at 3 weeks. This elevated difference between treatment and vehicle group demonstrated that the gel delivery system was able to preserve, for up to 3 weeks, the bioactivity of the released CD-NP.

In the predicate study, an excess of CD-NP was injected into rats to demonstrate sustained release of CD-NP over a 3-week release duration (Lim et al., *J. Cardiac Failure*, 18:S63 (2012)). It was observed that at the 3 week time point, the pcGMP concentration reduced to a level not significantly different from the baseline despite the elevated pCD-NP conc. of 8,000±1115 pg/mL. It was postulated that a sustained delivery of high CD-NP concentration from the gel led to a constant high cGMP activation. This high activation rate may be deemed 'abnormal' by the body. As such, the drop in plasma cGMP was due to compensatory responses which intervene to regulate the abnormally high amount of pcGMP. Three such compensatory responses were identified. Firstly, down regulation of NPR-A/B receptors to reduce cGMP production; secondly, 'over-drive' of clearance NPR-C receptors may also assist in reducing pCD-NP level and thus lead to a reduction in cGMP activation. And thirdly, pcGMP could be lowered by increasing cGMP excretion via kidney filtration. This mechanism of reducing plasma cGMP was confirmed in the elevated urinary cGMP excretion.

Plasma CD-NP and cGMP data from this study support the above postulation. In this study, at 3 weeks, plasma CD-NP and cGMP was 5,000±505 pg/mL and 170±21.4 pmol/mL, respectively, while the 3 week plasma CD-NP and cGMP in the previous study was 8,000±1115 pg/mL and 110±35.4 pmol/mL. Comparing the two sets of data, a higher sustained CD-NP release (as shown in an elevated CD-NP level of ~8000 pg/mL) yielded a lower pcGMP conc., while a lowered CD-NP release (in present study) yielded a higher pcGMP conc. at 3 weeks. In this case, by having a reduced dosage, the suppression of cGMP activation was not as extensive, resulting in a higher pcGMP conc. at 3 weeks.

Urinary Output Evaluation

Figure 13:
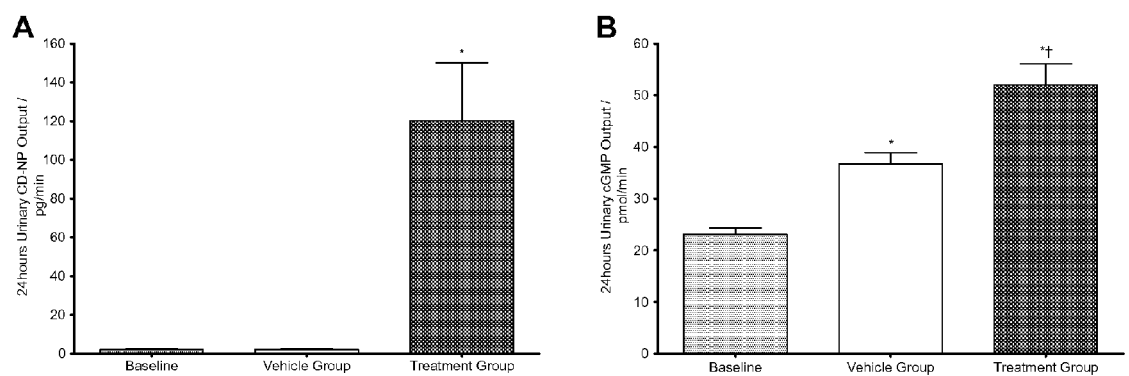
FIG. 13A is a graph plotting 24 hours urinary CD-NP output.
FIG. 13B is a graph plotting 24 hours urinary cGMP output. *P<0.05 vs. Baseline; †P<0.05 vs. Vehicle.

FIG. 13 illustrates the urinary CD-NP and cGMP outputs at 3 weeks. Baseline and vehicle group urinary CD-NP output was found to be similar at 2.0±0.23 pg/min and 2.1±0.14 pg/min, respectively. As expected, the urinary CD-NP output for treatment group was significantly different at 120±29.8 pg/min. High urinary CD-NP output suggests that at 3 weeks, there was still an excess of CD-NP being released from the gel as needed by the body.

Baseline, vehicle, and treatment group urinary cGMP outputs were found to be 23±1.2 pmol/min, 36±2.2 pmol/min, and 52±4.1 pmol/min, respectively. Both vehicle and treatment levels were significantly elevated as compared to the baseline. The treatment group also was significantly higher than that of the vehicle group.

The elevated urinary excretion of both CD-NP and cGMP demonstrated that the drug loading could potentially be reduced even further, provided that this did not affect the attenuation of the cardiac remodeling.

Cardiac Function and Structure Evaluation

Figure 14:
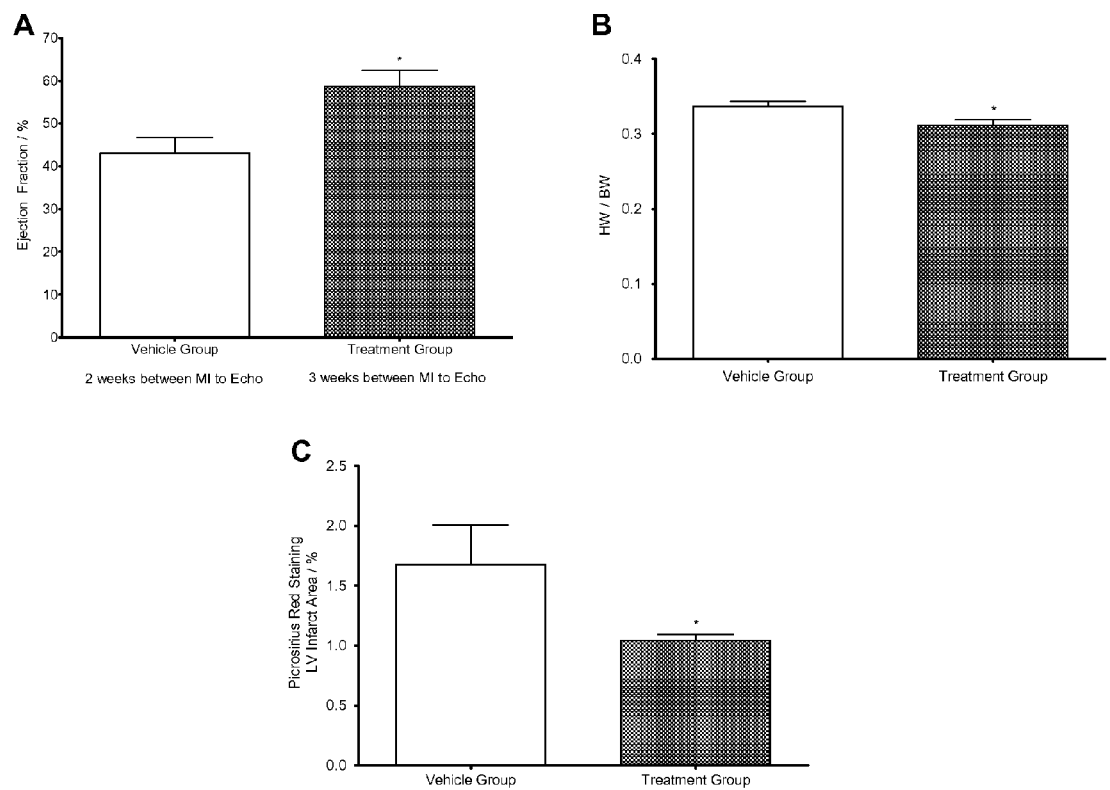
FIGS. 14A-C are graphs plotting ejection fraction (A), heart/body weight ratio (B), and LV cardiac fibrosis (C) for Treatment and Vehicle groups. *P<0.05, Treatment vs Vehicle

Cardiac function and structure between vehicle and treatment group was illustrated in FIG. 14. Left ventricular ejection fraction, assessed by conventional echocardiogram, was measured to be significantly different at 43±3.7% and 59±4.2% for vehicle and treatment groups. The heart/body weight ratios between vehicle and treatment groups were also significantly different at 0.337±0.007 and 0.312±0.008, respectively. More importantly, a significant reduction in fibrosis and collagen deposition in treatment group as compared to the vehicle group was observed. Picrosirius red staining for vehicle group was measured to be 1.7±0.3% as compared to 1.0±0.1% for the CD-NP-treated group.

Deterioration of both cardiac hemodynamic function and cardiac fibrosis is associated with cardiac remodeling. Cardiac remodeling, in this case, was initiated with the ligation of LAD at the start of the study.

Data from the vehicle group illustrated a marked decrease in heart function, evident from the reduced ejection fraction and hypotensive state experienced by rat. In addition to the cardiac functions, a higher heart/body weight ratio and the presence of marked fibrosis and collagen deposition in the left ventricular also illustrated the remodeling mechanism in acute myocardial infarction. The CD-NP treated group, on the other hand, was found to perform significantly better in most aspects of the analysis performed. This clearly demonstrated the cardio-protective effects of CD-NP.

With the delivery systems provided herein (e.g., a CD-NP delivery system), the constant release of a natriuretic polypeptide (e.g., CD-NP) from the gel depot over a 3 week duration demonstrated a distinct improvement in both functionality and structural integrity of the heart. Both systolic and diastolic functions exhibited a better cardiac function as shown by the better ejection fraction. Although ejection fraction was not completely preserved, it exhibited an improvement. This also was revealed by the significantly higher BP as compared to vehicle. Structurally, the remodeling process also was lessened, as revealed by the heart/body weight ratios in the treated rats which were found to be significantly lowered than that of the untreated rats. This, also, was supported with the reduction in fibrosis and collagen deposition.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A polymer gel composition comprising a natriuretic polypeptide, poly(lactic-co-glycolic acid), N-methyl-2-pyrrolidinone, and triacetin, wherein the poly(lactic-co-glycolic acid) of said composition has an intrinsic viscosity between 0.3 and 3 dL/g, and wherein said natriuretic polypeptide is released from said gel composition into a mammal's circulation over a period of time greater than 4 weeks, when said gel composition is delivered to said mammal.

2. The composition of claim 1, wherein the natriuretic polypeptide is CD-NP.

3. The composition of claim 1, wherein the natriuretic polypeptide comprises the amino acid sequence set forth in one of SEQ ID NOs:1-10.

4. The composition of claim 1, wherein the composition comprises from about 0.1 percent and 0.5 percent of the natriuretic polypeptide by weight.

5. The composition of claim 1, wherein the composition comprises from about 15 percent and 45 percent of the poly(lactic-co-glycolic acid) by weight.

6. The composition of claim 1, wherein the composition comprises from about 15 percent and 25 percent of the poly(lactic-co-glycolic acid) by weight.

7. The composition of claim 1, wherein the composition comprises from about 1 percent and 10 percent of triacetin by weight.

8. The composition of claim 1, wherein the composition comprises acid capped poly(lactic-co-glycolic acid).

* * * * *

```
                        SEQUENCE LISTING

<160> NUMBER OF SEQ ID NOS: 10

<210> SEQ ID NO 1
   <211> LENGTH: 28
   <212> TYPE: PRT
   <213> ORGANISM: Homo sapiens

<400> SEQUENCE: 1

Ser Leu Arg Arg Ser Ser Cys Phe Gly Gly Arg Met Asp Arg Ile Gly
   1               5                   10                  15

Ala Gln Ser Gly Leu Gly Cys Asn Ser Phe Arg Tyr
               20                  25

<210> SEQ ID NO 2
   <211> LENGTH: 32
   <212> TYPE: PRT
   <213> ORGANISM: Homo sapiens

<400> SEQUENCE: 2

Ser Pro Lys Met Val Gln Gly Ser Gly Cys Phe Gly Arg Lys Met Asp
   1               5                   10                  15

Arg Ile Ser Ser Ser Ser Gly Leu Gly Cys Lys Val Leu Arg Arg His
               20                  25                  30

<210> SEQ ID NO 3
   <211> LENGTH: 22
   <212> TYPE: PRT
   <213> ORGANISM: Homo sapiens

<400> SEQUENCE: 3

Gly Leu Ser Lys Gly Cys Phe Gly Leu Lys Leu Asp Arg Ile Gly Ser
   1               5                   10                  15

Met Ser Gly Leu Gly Cys
               20

<210> SEQ ID NO 4
   <211> LENGTH: 32
   <212> TYPE: PRT
   <213> ORGANISM: Homo sapiens

<400> SEQUENCE: 4

Thr Ala Pro Arg Ser Leu Arg Arg Ser Ser Cys Phe Gly Gly Arg Met
   1               5                   10                  15

Asp Arg Ile Gly Ala Gln Ser Gly Leu Gly Cys Asn Ser Phe Arg Tyr
               20                  25                  30

<210> SEQ ID NO 5
   <211> LENGTH: 38
   <212> TYPE: PRT
```

<213> ORGANISM: Dendroaspis angusticeps

<400> SEQUENCE: 5

Glu Val Lys Tyr Asp Pro Cys Phe

```
                    20                  25                  30
His

<210> SEQ ID NO 10
<211> LENGTH: 33
<212> TYPE: PRT
<213> ORGANISM: Artificial Sequence
<220> FEATURE:
<223> OTHER INFORMATION: synthetic polypeptide

<400> SEQUENCE: 10

Arg Met Asp Arg Ile Gly Leu Ser Lys Gly Cys Phe Gly Leu Lys Leu
 1               5                  10                  15

Asp Arg Ile Gly Ser Met Ser Gly Leu Gly Cys Lys Val Leu Arg Arg
            20                  25                  30

His
```